US010029044B2

United States Patent
Van Thiel (10) Patent No.: US 10,029,044 B2
(45) Date of Patent: Jul. 24, 2018

(54) APPARATUS FOR TREATING A TENNIS ELBOW BY MEANS OF PERCUTANEOUS INTERVENTION, AS WELL AS A HOLDER FOR USE WITH SUCH AN APPARATUS

(71) Applicant: Robert Cornelis Van Thiel, Teteringen (NL)

(72) Inventor: Robert Cornelis Van Thiel, Teteringen (NL)

(73) Assignee: ITEC MEDICAL B.V., Portugaal (NL)

( * ) Notice: Subject to any disclaimer, the term of this patent is extended or adjusted under 35 U.S.C. 154(b) by 945 days.

(21) Appl. No.: 14/325,577

(22) Filed: Jul. 8, 2014

(65) Prior Publication Data

US 2016/0008535 A1   Jan. 14, 2016

(51) Int. Cl.
| | |
|---|---|
| A61M 5/00 | (2006.01) |
| A61M 5/32 | (2006.01) |
| A61B 17/20 | (2006.01) |
| A61H 39/08 | (2006.01) |
| A61B 17/34 | (2006.01) |

(52) U.S. Cl.
CPC ........... *A61M 5/008* (2013.01); *A61B 17/205* (2013.01); *A61B 17/3403* (2013.01); *A61H 39/08* (2013.01); *A61M 5/3295* (2013.01); *A61B 2017/3405* (2013.01); *A61B 2017/3409* (2013.01); *A61H 2201/0173* (2013.01); *A61H 2201/1635* (2013.01); *A61H 2205/06* (2013.01); *A61M 2209/082* (2013.01); *A61M 2209/084* (2013.01)

(58) Field of Classification Search
CPC . A61M 5/008; A61M 5/46; A61B 2017/3405; A61B 2017/3409; A61H 39/08
See application file for complete search history.

(56) References Cited

U.S. PATENT DOCUMENTS

| | | | | |
|---|---|---|---|---|
| 5,034,003 A | * | 7/1991 | Denance | A61M 5/20 604/117 |
| 5,472,427 A | * | 12/1995 | Rammler | A61B 17/0281 604/164.01 |
| 2006/0128919 A1 | * | 6/2006 | Okamoto | C08L 101/10 528/25 |

FOREIGN PATENT DOCUMENTS

| | | | | |
|---|---|---|---|---|
| CH | 396311 | 7/1965 | | |
| EP | 2377475 | 10/2011 | | |
| EP | 2377475 A1 | * 10/2011 | ........... | A61B 17/205 |

(Continued)

*Primary Examiner* — Andrew Gilbert
*Assistant Examiner* — William Frehe
(74) *Attorney, Agent, or Firm* — Young & Thompson (57) ABSTRACT

An apparatus for treating a tennis elbow by percutaneous intervention, includes:
  a body having an actuating element,
  a fixing part arranged to fixably position the body,
  a positioning device connected to the body, including a positioning part moveable by the actuating element,
  a holder releasably connected to the positioning part, and including a top part for the releasable connection to the positioning part and a bottom part defining a support surface for supporting an elbow tendon region of a person to be treated, the support surface, the top and bottom parts being connected by one or more connecting members, the holder including a holder part with a number of penetration elements arranged thereon, wherein the top and bottom parts are spaced-apart at such a distance that, before penetration of the elbow tendon, the penetration tips of the penetration elements are covered by the bottom part.

13 Claims, 3 Drawing Sheets

(56) References Cited

FOREIGN PATENT DOCUMENTS

| GB | 941685   | * 10/1961 | ........... A61B 17/205 |
| GB | 941685   | * 11/1963 | |
| GB | 941685 A | * 11/1963 | ........... A61B 17/205 |

* cited by examiner

APPARATUS FOR TREATING A TENNIS ELBOW BY MEANS OF PERCUTANEOUS INTERVENTION, AS WELL AS A HOLDER FOR USE WITH SUCH AN APPARATUS

FIELD OF THE INVENTION

The present invention relates to an apparatus for treating a tennis elbow by means of percutaneous intervention.

BACKGROUND OF THE INVENTION

Approximately 1-3% of the general population is affected by a tennis elbow. In particular the age group between 35-54 years of age suffers from this complaint, with men and women both being affected to the same degree by this medical condition. Contrary to popular belief, a tennis elbow is not usually caused by playing tennis. This cause only accounts for 5-10% of patients.

It is known that a tennis elbow (medical term: epicondylitis lateralis) involves a degeneration of the tendon of the muscle known as "musculus extensor carpi radialis brevis" (ECRB).

The object of treating a tennis elbow is to alleviate the pain in the elbow and to return the elbow to its normal function as soon as possible. To this day, it is not known which type of treatment is most effective. The most commonly used treatments of a tennis elbow are: physiotherapy, a brace, immobilisation by putting the elbow in plaster, surgery during which cuts are made in the affected tendon, and percutaneous interventions. The latter treatment is discussed in more detail below.

In medical practice, it has been found that a treatment of the affected tendon in the case of a tennis elbow by means of various manual penetration operations of this tendon by means of a penetration means can be effective. Whether this so-called "percutaneous intervention" is more effective than surgery is not known, but it is less invasive which means that the patient can resume his/her activities after such an intervention much sooner than after surgery. These penetrations often are combined with injection of for instance corticosteroids, blood platelets, autologous blood, dextrose or hyaluronic acid.

However, with a percutaneous intervention, it is a problem to determine the exact position of the needle with respect to the patient, in order to ensure that the correct tissue is pierced and a correct position of the penetration means with respect to the patient's arm is achieved. As of yet, this treatment is often performed by hand and without ultrasound guidance.

In European patent publication EP 2,377,475, by the present applicant, an apparatus for treating tennis elbow is described for carrying out the percutaneous intervention of the elbow tendon in a much more convenient, standardized, fool-proof way.

From Swiss patent publication CH 396,311 a device is known aimed at stimulating the blood circulation in the skin by stimulating the skin with needles. The device is unsuitable for carrying out a controlled percutaneous intervention, however.

A drawback of the apparatus of EP 2,377,475 is that the positioning of the penetration means, both before and during penetration, requires a very high degree of accuracy. The known devices leave a lot to be desired in this respect. Another disadvantage of the known devices is that, before or after penetration, unwanted injuries can be sustained due to accidental touching of the sharp tips of the penetration means.

It is an object of the present invention to provide an apparatus for the treatment of a tennis elbow by means of percutaneous intervention, wherein a very high degree of accuracy is provided when positioning the penetration means, both before and during penetration. A further object of the invention is to provide an abovementioned apparatus, wherein unwanted injuries, before or after penetration, due to accidental touching of the tips of the penetration means are prevented.

SUMMARY OF THE INVENTION

To this end, the apparatus according to the invention comprises:
- a body having an actuating means for operating the apparatus,
- a fixing part arranged to fixably position the apparatus body with respect to its surroundings,
- a positioning device connected to the body, comprising a positioning part moveable upon actuation of the actuating means,
- a holder releasably connected to the positioning part of the positioning device, wherein the holder comprises a top part for the releasable connection to the positioning part and a bottom part defining a support surface for being supported on an elbow tendon region of a person to be treated, the support surface during use at least partially extending along the elbow tendon region, the top part and the bottom part being spaced-apart and being connected by one or more connecting members, wherein the holder comprises a holder part with a number of penetration means arranged thereon in a pattern, wherein the top part and the bottom part are spaced-apart at such a distance that, before penetration of the elbow tendon, the penetration tips of the penetration means are covered by the bottom part,
- the holder part being moveable along the connecting members upon actuation of the actuating means, in the direction of the bottom part, wherein the connecting members act as guidance members for the holder part, such that the penetration means are controllably moved towards the elbow tendon region for penetration of the elbow tendon.

By providing the holder with the above connecting members, the penetration means can be conveniently and controllably guided towards the bottom part and eventually the elbow tendon to be penetrated. The bottom part, suitable for being supported on the elbow tendon region and partially extending along the elbow tendon region, i.e. along the skin surface directly above the elbow tendon, provides further steady support during penetration. Furthermore, due to the top part and the bottom part being spaced-apart at such a distance that the penetration tips of the penetration means are covered by the bottom part, unwanted injuries due to accidental touching of the sharp tips of the penetration means are prevented. In the context of this patent application, the covering of the penetration means by the bottom part after penetration may be referred to as 'recapping'.

In an embodiment, the apparatus is provided with the bottom part of the holder comprising a number of through-openings, matching the pattern, for allowing the penetration means to pass there through during penetration. This provides even better stability and guidance of the penetration means during penetration.

Moreover, the apparatus can be provided with the holder part and the top part being fixedly connected to each other and the top part being slideably arranged on the connecting members near an upper end of the connecting members and a lower end of the connecting members is fixedly connected to the bottom part, wherein the positioning part, the top part and the holder are slid towards the bottom part upon actuation of the actuating means.

In an embodiment of the invention, the positioning part comprises a height adjustment device for adjusting the penetration depth of the penetration means with respect to the bottom part and the elbow tendon region, prior to operation of the actuating means. Thus, the penetration depth of the subsequent penetration can be set with a very high level of accuracy.

To this end, the height adjustment device can comprise a height adjustment screw, having a head part and a threaded part, a lower end of the threaded part being connected to the upper end of one of the connecting members, the threaded part being aligned with the connecting member with its screw axis, such that the positioning part can slide along the threaded part and the connecting member in a single sliding movement, the thread of the threaded part engaging the positioning part, wherein, before operation of the actuating means, upon downward adjustment of the head part of the height adjustment screw, the penetration depth is decreased, due to the stroke of the sliding movement becoming shorter, whereas upon upward adjustment of the head of the height adjustment screw, the penetration depth is increased, due to the stroke of the sliding movement becoming longer.

An embodiment relates to an abovementioned apparatus, wherein the positioning part further comprises a suspension device connected to the positioning part on the one hand and one of the connecting members on the other hand for damping sudden movements of the connecting member. This is especially useful for instance when a patient moves his arm against the bottom plate by accident.

An embodiment relates to an abovementioned apparatus, wherein the holder part comprises one or more openings fluidly connected to one or more channels inside the holder part, the one or more channels being in fluid connection to a top part of the penetration means for allowing the injection of a fluid via the openings through the penetration means into the elbow tendon. Thus, during penetration, medications in fluid form can be injected into the elbow tendon.

An embodiment relates to an abovementioned apparatus, wherein an upper surface of the top part and a lower surface of the bottom part of the holder comprise a sealing protecting film. In this manner, the holder can be kept safe and clean from dirt. Furthermore, the film can be used for initial connection of the top plate to an upper part of a connecting member. Upon removal of the film, a sliding movement of the top part along the connecting member can be realized.

Another aspect of the invention concerns a holder suitable for releasable connection to the positioning part of the positioning device of the apparatus according to any one of the preceding claims, wherein the holder comprises a top part for the releasable connection to the positioning part and a bottom part defining a support surface for being supported on an elbow tendon region of a person to be treated, the support surface during use at least partially extending along the elbow tendon region, the top part and the bottom part being spaced-apart and being connected by one or more connecting members, wherein the holder comprises a holder part with a number of penetration means arranged thereon in a pattern, the holder part being moveable along the connecting members upon actuation of the actuating means, in the direction of the bottom part, wherein the connecting members act as guidance members for the holder part, such that the penetration means are controllably moved towards the elbow tendon region for penetration of the elbow tendon.

An embodiment relates to an abovementioned holder, wherein the holder part comprises one or more openings fluidly connected to one or more channels inside the holder part, the one or more channels being in fluid connection to a top part of the penetration means for allowing the injection of a fluid via the openings through the penetration means into the elbow tendon.

An embodiment relates to an abovementioned holder, wherein an upper surface of the top part or a lower surface of the bottom part of the holder comprise a sealing protecting film.

Other aspects, features and details of the present invention will be readily understood by reference to the following detailed description of preferred embodiments of the apparatus and holder according to the invention, taken in conjunction with the drawings.

DETAILED DESCRIPTION

The invention will be explained in more detail with reference to one or more embodiments by means of figures, in which.

Figure 1:
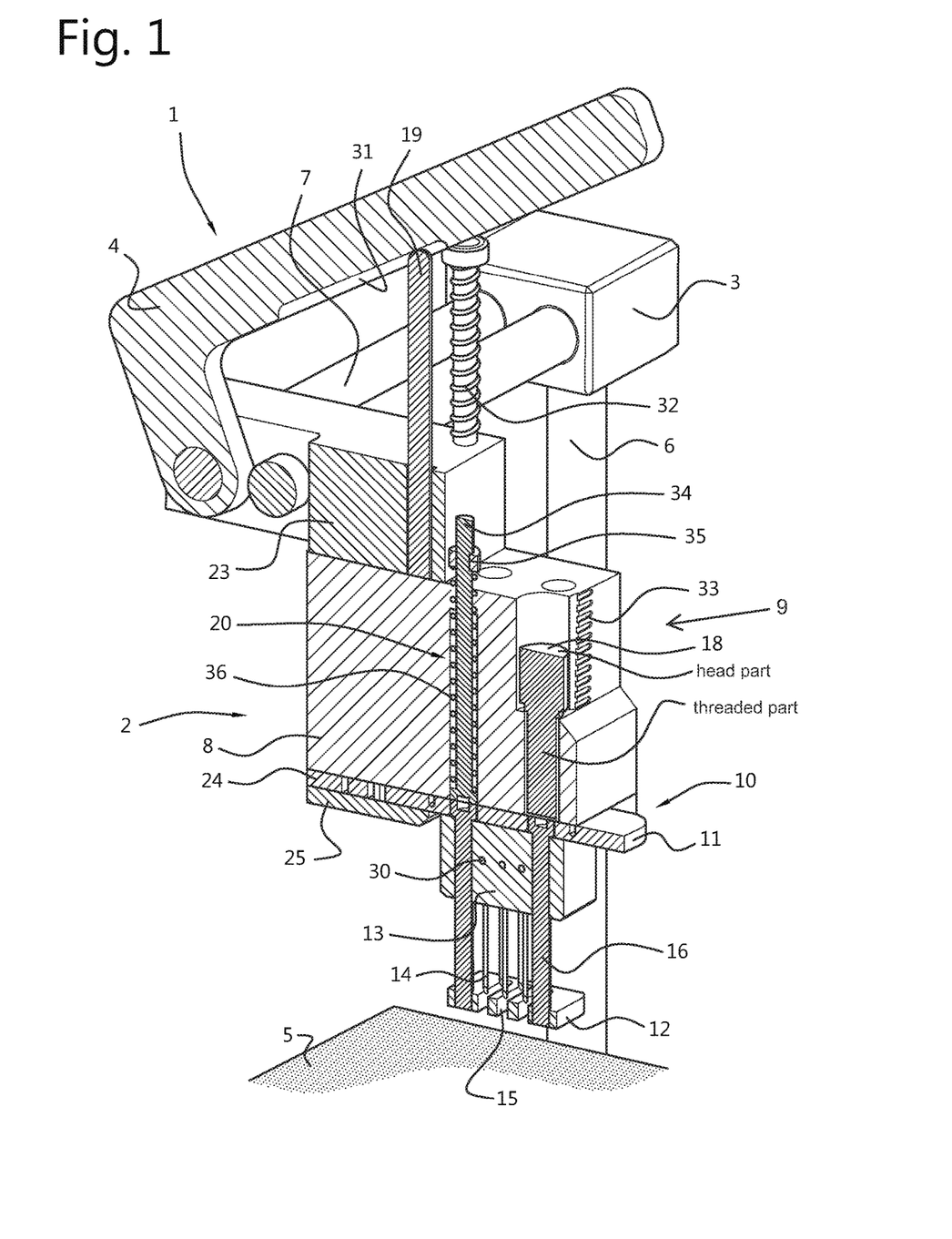
FIG. 1 shows a perspective view of an embodiment of an apparatus according to the invention in cross-section of, FIG. 2 shows a perspective view of an embodiment of a holder according to the invention.

FIG. 1 shows a perspective view of an apparatus according to the invention in cross-section, i.e. a cross-section along a vertical plane. In FIG. 1 the apparatus 1 comprises an apparatus body 2 with a coupling part 3 which connects a vertical fixing rod 6 and a pair of horizontal rods 7 arranged perpendicular to the fixing rod 6. The fixing rod 6 connects the apparatus 1 to its surroundings such as a treatment table 5, or the like. Alternatively, the fixing rod 6 can be embodied to be connected to a wall in the treatment space. The coupling part 3 allows rotation of the rods 7 in a plane perpendicular to the fixing rod 6. Of course, the coupling part 3 may be further adapted to provide height adjustment or rotation of the rods 7 in a vertical plane. Other translational or rotating movements are also conceivable for the coupling part 3. One end of the rods 7 is connected to the coupling part 3 while an opposing end is connected to a mounting block 23. A handle 4 is hingeably attached to the mounting block 23. The handle 4 is rotatable in a vertical plane. As shown, it is conceivable to attach the handle 4 to the respective opposing end of one of the rods 7. If desired, the rod 7 may rotate along with the handle 4 movement. The rods 6, 7 preferably have a circular cross-section. In a preferred embodiment, the construction with the fixing rod 6, the coupling part 3 and the rods 7 is fully symmetrical with respect to the vertical cross-sectional plane.

Preferably, the patient's arm is received in a special frame or plate arranged on the table 5 to allow the patient's arm to remain static during penetration.

As stated, FIG. 1 shows the handle 4 being mounted on a mounting block 23 extending. By means of example, the mounting block 23 may have a cubic, trapezoidal or similar shape. As illustrated, the mounting block 23 has a rear portion having a pair of horizontal through-holes the ends of the rods 7 are positioned. The handle 4 can be an L-shaped handle 4 wherein the short part of the 'L' is rotatably connected to one end of one of the horizontal rods 7, while the long part of the 'L' can be grabbed by a person's hand for pushing or pulling. The length ratio of the short part versus the long part may for instance be 1:3-1:4. Thus, sufficient torque and, more importantly, downwards force is provided for penetrating the patient's elbow tendon (region) when pushing the handle 4 in a downwards direction. The above ratios also cause the amount of torque and downwards force to be well-controllable.

As can be seen, the long part of the 'L' comprises a groove 31 extending along its downward edge. The groove 31 has a length of approximately ¼-½, such as ⅓, of the length of the long part. An upper end of a vertical, elongated force transfer member 19 is slideably arranged in the groove 31. The force transfer member 19 is vertically slideably arranged in the mounting block 23. The upper end of the force transfer member 19 projects from an upper surface of the mounting block 23. The length of the force transfer member 19 and the length of the groove 31, with which the force transfer member 19 cooperates, are preferably designed in such a way as to control and limit the downward movement of the handle 4 (and ultimately the vertical stroke of the penetration means, which will be explained later) when pushed downwards. In a preferred embodiment, a pair of such force transfer members 19 can be provided, each force transfer member 19 being arranged near a corner of the mounting block 23, i.e. each on one side of the cross-sectional plane as to achieve a symmetrical force transfer arrangement. The top ends of the pair of force transfer members 19 can be connected by a horizontally arranged, elongated member (not shown) that receives the force from the handle 4 and transfers the force to the two force transfer members 19 to obtain an even force distribution. Preferably, the elongated member has a cylindrical shape. The design of the groove 31 is to be adapted accordingly.

In the exemplary embodiment of FIG. 1, the mounting block 23 is connected to a positioning device 9 comprising a positioning block 8 by means of a pair of retaining means (of which only one is shown since FIG. 1 shows a cross-section) embodied as spring members 32, provided at each side of the force transfer member 19. The spring members 32 each comprise a central, vertical part, protruding through the mounting block 23 in downwards direction and connecting to the positioning block 8. The outer part of the central, vertical part is provided with a coil spring extending downwards along the central, vertical part and arranged between a top part of the central part and the upper surface of the mounting block 23. The spring members 32 allow the positioning block 8 to move downwards with respect to the mounting block 23. With increasing downwards movement/stroke, the spring force will increase, causing the positioning block 8 to have an increasing 'urge' to move upwards back to the mounting block 23. The spring tension of the spring members 32 is preferably adjustable, e.g. by adjusting the vertical position of the top part of the central part with respect to the mounting block 23.

Figure 3A:
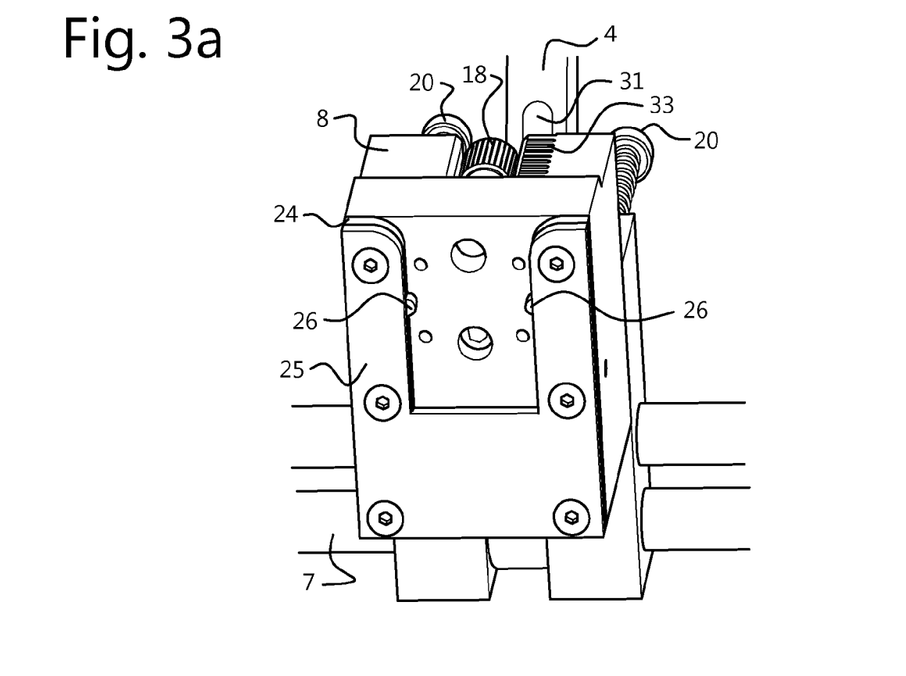
FIG. 3*a* shows a perspective bottom view of an embodiment of a positioning device according to the invention having a first and a second connecting plate in assembled state.
Figure 3B:
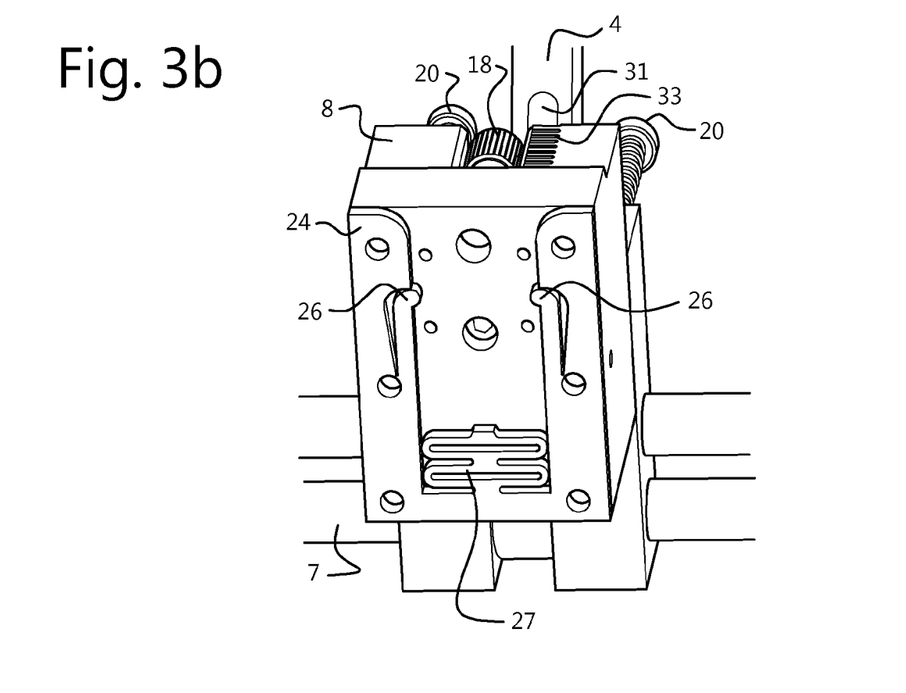
FIG. 3*b* shows a perspective view of n embodiment of a positioning device to the invention, wherein the second connecting plate is removed.

The positioning block 8 comprises several vertical through-holes in which further devices, parts or equipment can be inserted, for instance to cooperate with the holder 10 arranged at a lower side of the positioning block 8. As illustrated, one of the through-holes of the positioning block 8 is provided with a height adjustment device 18. The respective through-hole has a sideways opening such that the height adjustment device 18 can be manipulated or otherwise operated. The height adjustment device 18 comprises a threaded part being inserted into the mentioned through-hole of the positioning block 8, while the top part or head part has a serrated outer surface for providing better rip upon rotation of the head part, as best seen in FIGS. 3a and 3b. The head part functions as a travel limiter for the sliding movement and thus the penetration depth, i.e. blocks the positioning block 8 from moving further upwards along the connection member 16 and the threaded part of the height adjustment device 18 when the desired penetration depth is achieved.

Moreover, next to the longitudinal aperture wherein the height adjustment device 18 is located, the positioning device 9 is provided with height indication marks 33 along one of its external side walls.

The positioning block 8 further comprises a suspension device 20 located in one of its through holes. As illustrated, the suspension device 20 comprises an elongated rod 34 having a spring element 36 arranged along its outer surface 34, and a closing element 35 in a form of a screw nut. The suspension device 20 dampens movements of a bottom part (end cap) 12 of the holder 10 with respect to the positioning block 8, in vertical direction (for instance when the patient accidentally bumps upwards against the bottom plate 12 with his or her arm).

Furthermore, the embodiment of the apparatus illustrated in FIG. 1 comprises a holder 10 which is releasably connected to the positioning block 8. As shown, the holder 10 comprises a top part 10 and a bottom part 12 being connected to each other by means of a couple of connecting members 16 in the form of rods. A holder part 13 is connected to the lower surface of the top part 11. The holder part 13 comprises a number of penetration means 14 in the form of needles 14 arranged in a pattern, such as in a number of rows, for instance 2 or 3 rows of 4 or 5 needles each. The needles can be arranged with their upper ends in a solid, preferably block-shaped element, for instance made of plastic. The holder part 13 further comprises a number of (sideways) openings 30 which connect to internal holder channels, which in turn are in fluid connection to the needles 14 and their (hollow) penetration tips. A syringe can for instance be plugged into the openings 30 for injecting medications, such as steroids, pain killers, anti-inflammatories, et cetera. However, it is conceivable that only one opening 30 will actually be used for receiving a syringe, whereas the other openings are closed-off. Thus, sufficient build-up of fluid pressure is achieved within the internal holder channels. Optionally, the internal holder channels are aligned with and fluidly connected to one or more of the openings 30 to allow both the respective internal holder channel and the respective opening to be drilled in a single drilling action.

The bottom part 12 of the holder 10 has the form of a (bottom) plate 12 comprising a number of openings 15 matching the pattern of the needles 14 for allowing the needles 14 to pass through the openings 15 during penetration of an elbow tendon underneath the bottom plate 12. It should be noted that before use, i.e. before the holder 10 is installed in the positioning block 8, the upper ends of the connecting members 16 are fixedly connected to the top plate 11, e.g. via the use of a sticky foil or film arranged over the top surface of the top plate 11. The lower ends of the connecting members 16 are fixedly attached to the bottom plate 12, before as well as during use.

During use (for instance after removing the aforementioned sticky foil), the top plate 11 and the rest of the holder 10 can slide in vertical direction along the connecting members 16. It should furthermore be noted that the aforementioned suspension device 20 as well as the height adjustment device 18 are vertically aligned with both connecting members 16 to facilitate the sliding movement. Furthermore, at the respective contact points between the upper parts of the connecting members 16 and the lower ends of both the suspension device 20 and the height adjustment device 18, the positioning block 8, both the connecting members 16, the suspension device 20 and the height adjustment device 18 are designed in such a way (especially with respect to their diameter) that the holder 10 (especially the top plate 11) can effortlessly slide up and down along the connecting members 16 past the contact points.

The holder 10 is releasably connected to the positioning block 8 by means of a first connecting plate 24 and a second connecting plate 25 which can be best illustrated and explained with reference to FIGS. 3a and 3b.

Figure 2:
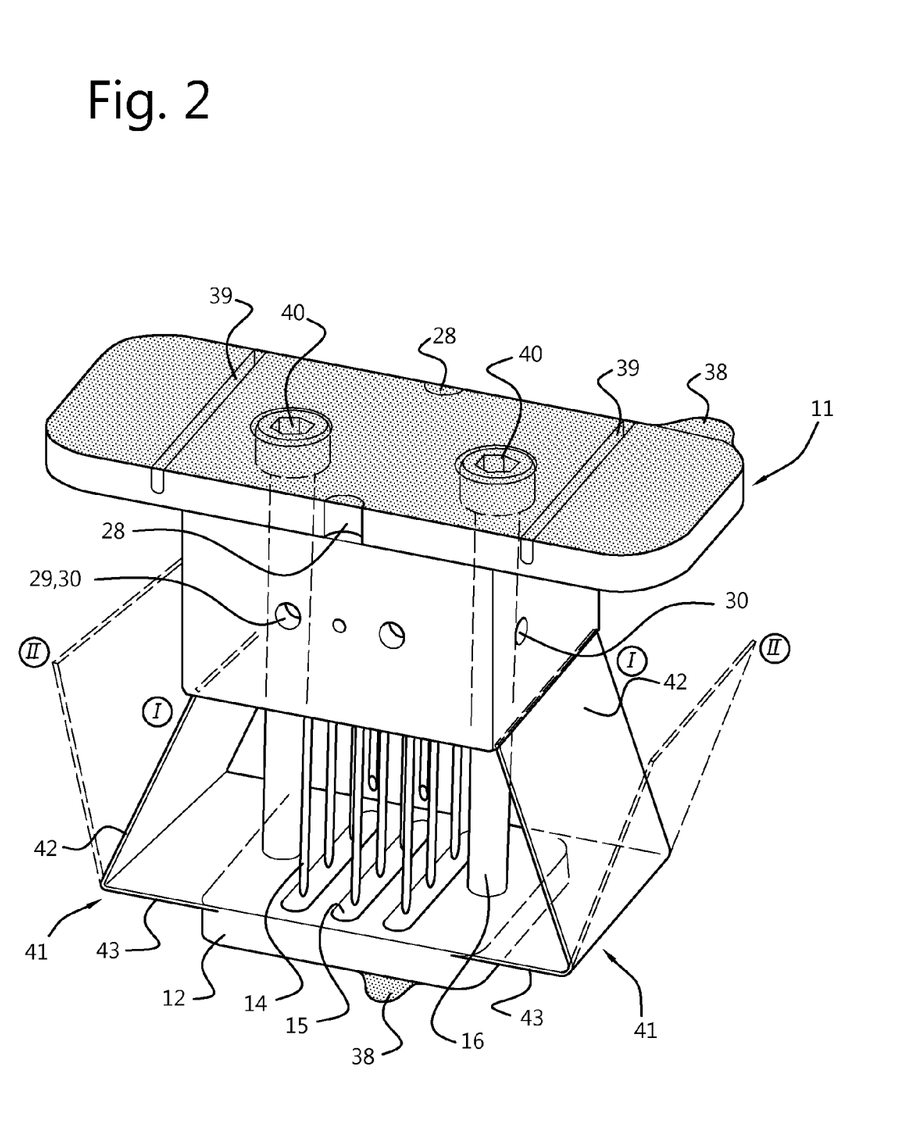

FIG. 2 shows the holder 10 according to the invention in detail, wherein the top and bottom plates 11, 12 comprise a sealing protecting film 38 for protecting the exposed surfaces of the plates 11, 12 before the use of the holder 10. As illustrated, the sealing protecting film 38 comprises a protruding tap for easy removal of said sealing protecting film 38. As can be seen, the top plate 11 comprises a top surface having a symmetrical structure, with a rectangular shape and rounded corners. On both sides of the longitudinal edges of the top plate 11, a groove 28 can be found. Advantageously, the top surface may be provided with a pair of breaking lines 39. After use of the holder 10, the holder 10 can only be removed from the connecting plate 24 by breaking the top plate 11, along one end of the top plate 11, along the respective breaking line 39. In this way, accidental re-use is prevented. Of course, other options are also conceivable, such as causing the bottom plate 12 to 'lock' after the penetration. In a preferred embodiment, the bottom plate 12 is provided with an additional blocking plate 41, having a base plate 43 connected to the bottom plate 12 and/or the connecting members 16, and extending in the same plane as the bottom plate 12. The opposing horizontal ends of the base plate 43 are provided with foldable parts 42, foldable around a horizontal axis. In a first (inward) folding position I, the foldable parts 42 prevent the holder 10 from moving downwards as the free ends of the foldable parts 42 block such movement. In a second (outward) folding position II, the holder 10 can move up and down freely. The second folding position II will be the default position when the penetration is carried out. After the penetration, the foldable parts 42 will be folded to the first position I to block further movement of the holder 10. Thus, re-use is prevented and the penetration means or needles 14 are 'recapped' preventing injuries from occurring due to accidental touching of the needle tips.

On the bottom plate 12, another sealing protecting film 38 is provided, which can be removed before or after connecting the holder 10 to the positioning block 8 of the apparatus 1. When the user sees that a certain holder 10 does not comprise the sealing protecting film 38, the user knows (in a visual way) that the holder 10 has already been used before.

The top plate 11 further comprises a series of openings 40 in which the connecting members 16 are slideably arranged (provided the foil 38 is removed). As illustrated, the connecting members 16 comprise a bolt head having a hexagonal cross-section. Moreover, the holder part 13 as shown comprises a number of openings 29 which are meant to inject fluids that can be provided via the needles 14 when treating the elbow tendon of a patient.

In the illustrated exemplary embodiment, the bottom plate 12 comprises openings 15 matching the pattern of the needles 14. The openings 15 can act as guiding mechanism for guiding the needles through them. The shape of the openings 15 may advantageously correspond to the length and/or width of a row of needles. E.g. when using 3 rows of 4 needles, there may be 3 (parallel, elongated) openings 15, each opening 15 having a length of approximately the distance between the first and last needle in the row. Therein, the surface area affected by the needles/penetration means may advantageously have dimensions of 5-20 mm, such as 8-15 mm, by 20-30 mm to treat a tendon area large enough for effectively inciting the tendon to heal. The dimensions of the bottom plate 12 are, for example, set to a length of about 5-15 cm, such as 10 cm and a width of 2-7 cm, such as 5 cm, with the thickness being less important. It should be noted that the thickness is primarily important for giving the bottom plate 12 sufficient stiffness.

FIG. 3a shows a perspective bottom view of the positioning block 8 having the first connecting plate 24 and the second connecting plate 25 in assembled state. The first connecting plate 24 is sandwiched in-between the second connecting plate 25 and the lower surface of the positioning block 8. Both connecting plates 24, 25 have a U-shape. As illustrated, a pair of opposing spring locking elements 26 protrude inward from the inside of the U's legs (of the first connecting plate 24) to engage the grooves 28 of the top plate 11, as to retain the holder 10 for performing the percutaneous intervention. The holder 10 can not be removed without breaking the top plate 11 along the respective breaking line 39. The base part of the U-shape of the first connecting plate 24 is provided with a spring element 27 to provide spring counter-pressure when sliding the top plate 11 into the U-shaped connecting plate 24.

FIG. 3b shows a perspective bottom view of the positioning block 8 of FIG. 3a wherein the second connecting plate 25 is removed for clarity.

Thus, the invention has been described by reference to the embodiments discussed above. It will be recognized that these embodiments are susceptible to various modifications and alternative forms well known to those of skill in the art without departing from the spirit and scope of the invention. Accordingly, although specific embodiments have been described, these are examples only and are not limiting upon the scope of the invention.

REFERENCE NUMERALS

1. Apparatus
2. Apparatus body
3. Connector part
4. Handle
5. Treatment table
6. —
7. Horizontal rod
8. Positioning block
9. Positioning device
10. Holder
11. Top part
12. Bottom part
13. Holder part
14. Penetration means
15. Openings 16. Connecting members
17. —
18. Height adjustment device
19. Force transfer member
20. Suspension device
21. —
22. —
23. Mounting block
24. First connecting plate
25. Second connecting plate
26. Spring locking element
27. Spring element
28. Groove section
29. Openings
30. Channels
31. Groove
32. Threaded screw
33. Serrated marks
34. Rod
35. Closing element
36. Spring element
37. —
38. Sealing protecting film
39. —
40. Openings
41. Blocking plate
42. Foldable part of blocking plate
43. Base part of blocking plate

The invention claimed is:

1. Apparatus (1) for treating a tennis elbow by means of percutaneous intervention, comprising:
    a body (2) having an actuating means (4) for operating the apparatus,
    a fixing part (6) arranged to fixably position the body (2) with respect to its surroundings,
    a positioning device (9) connected to the body (2), the positioning device (9) comprising a positioning block (8) moveable upon actuation of the actuating means (4),
    a holder (10), in a connected state releasably connected to the positioning block (8) and in a disconnected state being disconnected from the positioning block (8),
    wherein the holder (10) in the disconnected state comprises a top part (11) for the releasable connection to the positioning block (8) and a bottom part (12) defining a support surface for being supported on an elbow tendon region of a person to be treated, the support surface during use at least partially extending along the elbow tendon region, the top part (11) and the bottom part (12) being spaced-apart and being connected by one or more connecting members (16),
    wherein the holder (10) comprises a holder part (13) with a number of penetration means (14) arranged thereon in a pattern, wherein the top part (11) and the bottom part (12) are spaced-apart at such a distance that, before penetration of an elbow tendon and in the disconnected state, penetrating tips of the number of penetration means (14) are covered by the bottom part (12),
    the holder part (13) in the connected state being moveable along the one or more connecting members (16) upon actuation of the actuating means (4), in the direction of the bottom part (12), wherein the one or more connecting members (16) act as guidance members for the holder part (13), such that the number of penetration means (14) are controllably moved towards an elbow tendon region for penetration of the elbow tendon, the holder part (13) being non-movable along the one or more connecting members (16) in the disconnected state due to the bottom part (12) being provided with a blocking plate (41) extending between the bottom part (12) and the holder part (13) and/or an upper surface of the top part (11) comprising a sealing protecting film (38) connecting the upper surface of the top part (11) with the upper ends of the one or more connecting members (16) which extend through the top part (11), wherein the blocking plate (41) and/or the sealing protecting film (38) blocking movement of the holder part (13) towards the bottom part (12) in the disconnected state.

2. Apparatus according to claim 1, wherein the bottom part (12) of the holder (10) comprises a number of through-openings (15), matching the pattern, for allowing the number of penetration means (14) to pass there through during penetration.

3. Apparatus (1) according to claim 1, wherein the holder part (13) and the top part (11) are fixedly connected to each other and the top part (11) is slideably arranged on the one or more connecting members (16) near an upper end of the one or more connecting members (16) and a lower end of the one or more connecting members (16) is fixedly connected to the bottom part (12), wherein the positioning block (8), the top part (11) and the holder part (13) are slid towards the bottom part (12) upon actuation of the actuating means (4).

4. Apparatus (1) according to claim 1, wherein the positioning block (8) comprises a height adjustment device (18) for adjusting a penetration depth of the number of penetration means with respect to the bottom part (12) and the elbow tendon region, prior to operation of the actuating means (4).

5. Apparatus (1) according to claim 4, wherein the height adjustment device comprises a height adjustment screw, having a head part and a threaded part, a lower end of the threaded part being connected to the upper end of one of the one or more connecting members (16), the threaded part being aligned with the one or more connecting members (16) with its screw axis, such that the positioning block (8) can slide along the threaded part and the one or more connecting members (16) in a single sliding movement, a in a single sliding movement, the thread of the threaded part engaging the positioning block (8), wherein, before operation of the actuating means (4), upon downward adjustment of the head part of the height adjustment screw, the positioning block (8) is adjusted towards the bottom part (12) and the elbow tendon region.

6. Apparatus (1) according to claim 1, wherein the positioning block (8) further comprises a suspension device (20) connected to the positioning block (8) on the one hand and one of the one or more connecting members (16) on the other hand for damping sudden movements of the one or more connecting members (16).

7. Apparatus (1) according to claim 1, wherein the holder part (13) comprises one or more openings (29) fluidly connected to one or more channels (30) inside the holder part (13), the one or more channels (30) being in fluid connection to a top part of the number of penetration means (14) for allowing an injection of a fluid via the openings (29) through the number of penetration means (14) into the elbow tendon.

8. Apparatus (1) according to claim 1, wherein the blocking plate (41) extending between the bottom part (12) and the holder part (13) blocks movement of the holder part (13) towards the bottom part (12) in the disconnected state.

9. Apparatus (1) according to claim 2, wherein the holder part (13) and the top part (11) are fixedly connected to each other and the top part (11) is slideably arranged on the one or more connecting members (16) near an upper end of the one or more connecting members (16) and a lower end of the one or more connecting members (16) is fixedly connected to the bottom part (12), wherein the positioning block (8), the top part (11) and the holder (13) are slid towards the bottom part (12) upon actuation of the actuating means (4).

10. A holder (10) that, in connected state, is releasably connected to the positioning block (8) of the positioning device (9) of the apparatus according to claim 1 and in a disconnected state is disconnected from the positioning block (8),
- wherein the holder (10) in the disconnected state comprises a top part (11) for the releasable connection to the positioning block (8) and a bottom part (12) defining a support surface for being supported on an elbow tendon region of a person to be treated, the support surface during use at least partially extending along the elbow tendon region, the top part (11) and the bottom part (12) being spaced-apart and being connected by one or more connecting members (16),
- wherein the holder (10) comprises a holder part (13) with a number of penetration means (14) arranged thereon in a pattern, the holder part (13) being moveable along the one or more connecting members (16) upon actuation of the actuating means (4), in the direction of the bottom part (12), wherein, before penetration of the elbow tendon and in the disconnected state, penetration tips of the number of penetration means (14) are covered by the bottom part (12), and in the connected state the connecting members (16) act as guidance members for the holder part (13), such that the number of penetration means (14) are controllably moved towards the elbow tendon region for penetration of the elbow tendon, the holder part (13) being non-movable along the one or more connecting members (16) in the disconnected state due to a blocking plate (41) provided at the bottom part (12) blocking movement of the holder part (13) towards the bottom part (12), and/or a sealing protecting film (38) connecting an upper surface of the top part (11) with upper ends of one or more connecting members (16) extending through the top part (11),
- wherein the blocking plate (41) extends between the bottom part (12) and the holder part (13) thereby blocking movement of the holder part (13) towards the bottom part (12) in the disconnected state, and/or the sealing protecting film (38) connecting the upper surface of the top part (11) with the upper ends of one or more connecting members (16) extending through the the top part (11) thereby blocking movement of the holder part (13) towards the bottom part (12) in the disconnected state.

11. Holder (10) according to claim 10, wherein the holder part (13) comprises one or more openings (29) fluidly connected to one or more channels (30) inside the holder part (13), the one or more channels (30) being in fluid connection to a top part of the number of penetration means (14) for allowing an injection of a fluid via the openings (29) through the number of penetration means (14) into the elbow tendon.

12. Apparatus (1) according to claim 1, wherein the blocking plate (41) extends between the bottom part (12) and the holder part (13) thereby blocking movement of the holder part (13) towards the bottom part (12) in the disconnected state, and the sealing protecting film (38) connecting the upper surface of the top part (11) with the upper ends of one or more connecting members (16) extending through the top part (11) thereby blocking movement of the holder part (13) towards the bottom part (12) in the disconnected state.

13. Holder (10) according to claim 11, wherein the blocking plate (41) extending between the bottom part (12) and the holder part (13) blocks movement of the holder part (13) towards the bottom part (12) in the disconnected state.

* * * * *